United States Patent [19]

Niewöhner et al.

[11] Patent Number: 4,882,353

[45] Date of Patent: Nov. 21, 1989

[54] CHROMAN DERIVATIVES FOR COMBATING THROMBOSIS AND ASTHMA

[75] Inventors: Ulrich Niewöhner, Wermelskirchen; Franz-Peter Hoever, Cologne; Folker Lieb, Leverkusen; Hermann Oediger, Cologne; Ulrich Rosentreter, Wuppertal; Horst Böshagen, Haan; Elisabeth Perzborn, Wuppertal; Volker-Bernd Fiedler, Leverkusen; Friedel Seuter, Wuppertal, all of Fed. Rep. of Germany

[73] Assignee: Bayer Aktiengesellschaft, Leverkusen, Fed. Rep. of Germany

[21] Appl. No.: 263,143

[22] Filed: Oct. 26, 1988

[30] Foreign Application Priority Data

Nov. 3, 1987 [DE] Fed. Rep. of Germany ....... 3737195

[51] Int. Cl.$^4$ ..................... A61K 31/35; C07D 311/04
[52] U.S. Cl. .................................... 514/456; 549/404; 549/406; 549/407
[58] Field of Search ....................... 549/404, 406, 407; 514/456

[56] References Cited

U.S. PATENT DOCUMENTS

4,210,663  7/1980  Belletire ............................. 549/407

FOREIGN PATENT DOCUMENTS

3411993  3/1984  Fed. Rep. of Germany ...... 549/407

Primary Examiner—Mary C. Lee
Assistant Examiner—Robert C. Whittenbaugh
Attorney, Agent, or Firm—Sprung, Horn, Kramer & Woods

[57] ABSTRACT

For inhibiting thombocyte aggregation, vasodilating and bronchodilating, the new chroman derivatives of the formula

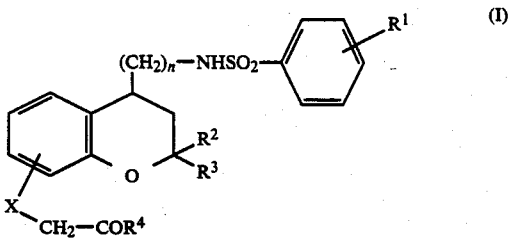

in which
$R^1$ stands for hydrogen, halogen, alkyl, hydroxyl, alkoxy, trifluoromethyl or cyano,
$R^2$ and $R^3$ are identical or different and stand for hydrogen, alkyl, cycloalkyl or aryl,
$R^4$ stands for hydroxyl, alkoxy, aryloxy, aralkoxy or for a group of the formula $-NR^5R^6$, where
$R^5$ and $R^6$ are identical or different and in each case denote hydrogen, alkyl, aryl or aralkyl,
X denotes a direct bond or an oxygen or sulphur atom, NH or N-alkyl, and
n denotes 0 or 1,
and their physiologically tolerable salts. Also new intermediates of the formulas

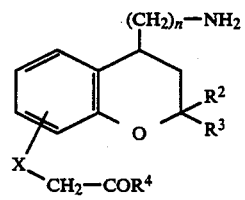

and

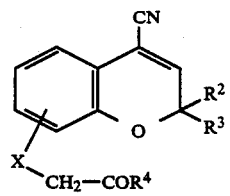

(IV)

11 Claims, No Drawings

CHROMAN DERIVATIVES FOR COMBATING THROMBOSIS AND ASTHMA

The invention relates to new chroman derivatives, a process for their preparation and their use in medicaments, in particular as agents for thrombosis and as medicaments against asthmatic diseases.

It is already known that certain chroman derivatives show interesting pharmaceutical actions. In German Offenlegungsschrift No. 3,411,993, for example, chroman derivatives having hypotensive action are described.

The invention relates to new chroman derivatives of the general formula (I)

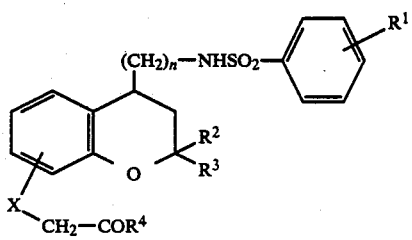

in which
$R^1$ stands for hydrogen, halogen, alkyl, hydroxyl, alkoxy, trifluoromethyl or cyano,
$R^2$ and $R^3$ are identical or different and stand for hydrogen, alkyl, cycloalkyl or aryl,
$R^4$ stands for hydroxyl, alkoxy, aryloxy, aralkoxy or for a group of the formula $-NR^5R^6$, where
$R^5$ and $R^6$ are identical or different and in each case denote hydrogen, alkyl, aryl or aralkyl,
X denotes a direct bond or an oxygen or sulphur atom, NH or N-alkyl, and
n denotes 0 or 1,
and their physiologically tolerable salts.

Alkyl in general stands for a hydrocarbon radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Aryl in general stands for an aromatic radical having 6 to about 12 carbon atoms. Preferred aryl radicals are phenyl, naphthyl and biphenyl.

Aralkyl in general stands for an aryl radical having 7 to 14 carbon atoms which is bonded via an alkylene chain. Aralkyl radicals having 1 to 6 carbon atoms in the aliphatic moiety and 6 to 12 carbon atoms in the aromatic moiety are preferred. The following aralkyl radicals may be mentioned as examples: benzyl, naphthylmethyl, phenethyl and phenylpropyl.

Alkoxy in general stands for a straight-chain or branched hydrocarbon radical having 1 to 12 carbon atoms which is bonded via an oxygen atom. Lower alkoxy having 1 to about 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

Aralkoxy in general stands for an aralkyl radical having 7 to 14 carbon atoms, the alkylene chain being bonded via an oxygen atom. Aralkoxy radicals having 1 to 6 carbon atoms in the aliphatic moiety and 6 to 12 carbon atoms in the aromatic moiety are preferred. The following aralkoxy radicals may be mentioned as examples: benzyloxy, naphthylmethoxy, phenethoxy and phenylpropoxy.

Halogen in general stands for fluorine, chlorine, bromine or iodine, preferably for fluorine, chlorine or bromine. Particularly preferably, halogen stands for fluorine or chlorine.

Preferred compounds are those of the general formula (I), in which
$R^1$ stands for hydrogen, fluorine, chlorine, bromine, iodine, methyl, ethyl, propyl, isopropyl, hydroxyl, methoxy, ethoxy, propoxy, isopropoxy, trifluoromethyl or cyano,
$R^2$ and $R^3$ are identical or different and stand for hydrogen, methyl, ethyl, propyl, isopropyl, cyclobutyl, cyclopentyl, cyclohexyl, cycloheptyl or phenyl,
$R^4$ stands for hydroxyl, methoxy, ethoxy, phenoxy, benzyloxy or for a group of the formula $-NR^5R^6$, where $R^5$ and $R^6$ are identical or different and in each case denote hydrogen, methyl, ethyl, phenyl or benzyl,
X stands for a direct bond or an oxygen or sulphur atom,
n stands for 0 or 1
and their salts.

The substances according to the invention surprisingly show a thrombocyte aggregation-inhibiting action and can be used for the treatment of thromboembolic diseases. Furthermore, they are bronchodilatory and can therefore also be used for the treatment of asthmatic diseases.

The chroman derivatives according to the invention can also exist in the form of their salts. In general, salts with inorganic or organic bases may be mentioned here.

In the context of the present invention, physiologically acceptable salts are preferred. Physiologically acceptable salts of the chroman derivatives can be metal or ammonium salts of the substances according to the invention which carry a free carboxyl group ($R^4$=OH). Particularly preferred are, for example, sodium salts, potassium salts, magnesium salts or calcium salts, and also ammonium salts which are derived from ammonia or organic amines, such as, for example, ethylamine, diethylamine, triethylamine, diethanolamine, triethanolamine, dicyclohexylamine, dimethylaminoethanol, arginine or ethylenediamine.

The new chroman derivatives can be present both as enantiomers, pairs of enantiomers or, in the presence of a further asymmetric centre in one of the radicals, as pairs of diastereomers.

The following new chroman or thiochroman derivatives may be mentioned as examples: 4-(phenylsulphonylaminomethyl)chroman-7-yloxyacetic acid, 4-(3-fluorophenylsulphonylaminomethyl)chroman-7-yloxyacetic acid, 4-(4-methylphenylsulphonylaminomethyl)chroman-7-yloxyactic acid, 4-(4-ethylphenylsulphonylaminomethyl)chroman-7-yloxyacetic acid, 4-(4-fluorophenylsulphonylaminomethyl)-2,2-dimethylchroman-7-yloxyacetic acid, 4-(phenylsulphonylaminomethyl)-2,2-dimethylchroman-7-yloxyacetic acid, 4-(4-methylphenylsulphonylaminomethyl)-2,2-dimethylchroman-7-yloxyacetic acid, 4-(phenylsulphonylaminomethyl)chroman-8-ylacetic acid, 4-(4-fluorophenylsulphonylaminomethyl)chroman-8-ylacetic acid, 4-(3-fluorophenylsulphonylaminomethyl)chroman-8-ylacetic acid, 4-(4-chlorophenylsulphonylaminomethyl)chroman-8-ylacetic acid, 4-(3-chlorophenylsulphonylaminomethyl)chroman-8-ylacetic acid, 4-(4-methylphenylsulphonylaminomethyl)chroman-8-ylacetic acid, 4-(4-trifluoromethylphenylsulphonylaminomethyl)chroman-8-ylacetic acid, 4-(phenylsulphonylaminomethyl)-2,2-dimethylchroman-8-ylacetic acid, 4-(4-fluorophenylsulphonylaminomethyl)-2,2-dimethylchroman-8-ylacetic acid, 4-(4-chlorophenylsulphonylaminomethyl)-2,2-dimethylchroman-8-ylacetic acid, 4-(4-methylphenylsulphonylaminomethyl)-2,2-dimethylchroman-8-ylacetic acid, 4-(phenylsulphonylaminomethyl)chroman-8-yloxyacetic acid, 4-(4-chlorophenylsulphonylaminomethyl)chroman-8-yloxyacetic acid, 4-(3-fluorophenylsulphonylaminomethyl)chroman-8-yloxyacetic acid, 4-(4-methylphenylsulphonylaminomethyl)chroman-8-yloxyacetic acid, 4-(4-ethylphenylsulphonylaminomethyl)chroman-8-yloxyacetic acid, 4-(4-methoxyphenylsulphonylaminomethyl)chroman-8-yloxyacetic acid, 4-(4-cyanophenylsulphonylaminomethyl)chroman-8-yloxyacetic acid, 4-(4-trifluorothylphenylsulphonylaminomethyl)chroman-8-yloxyacetic acid, 4-(phenylsulphonylaminomethyl)-2,2-dimethylchroman-8-yloxyacetic acid, 4-(4-fluorophenylsulphonylaminomethyl)-2,2-dimethylchroman-8-yloxyacetic acid, 4-(4-chlorophenylsulphonylaminomethyl)-2,2-dimethylchroman-8-yloxyacetic acid, 4-(phenylsulphonylaminomethyl)-2,2-spirocyclopentylchroman-8-yloxyacetic acid, 4-(4-fluorophenylsulphonylaminomethyl)-2,2-spirocyclopentylchroman-8-yloxyacetic acid, 4-(4-chlorophenylsulphonylaminomethyl)-2,2-spirocyclopentylchroman-8-yloxyacetic acid, 4-(phenylsulphonylaminomethyl)-2,2-dimethylchroman-7-ylacetic acid, 4-(3-fluorophenylsulphonylaminomethyl)-2,2-dimethylchroman-7-ylacetic acid, 4-(4-cyanophenylsulphonylaminomethyl)-2,2-dimethylchroman-7-ylacetic acid, 4-(4-methoxyphenylsulphonylaminomethyl)-2,2-dimethylchroman-7-ylacetic acid, 4-(4-fluorophenylsulphonylaminomethyl)-2-phenylchroman-7-yloxyacetic acid, 4-(phenylsulphonylamino)chroman-7-yloxyacetic acid, 4-(4-fluorophenylsulphonylamino)chroman-7-yloxyacetic acid, 4-(4-chlorophenylsulphonylamino)chroman-7-yloxyacetic acid, 4-(4-trifluoromethylphenylsulphonylamino)chroman-7-yloxyacetic acid, 4-(4-methylphenylsulphonylamino)chroman-7-yloxyacetic acid, 4-(3-fluorophenylsulphonylamino)chroman-7-yloxyacetic acid, 4-(phenylsulphonylaminomethyl)chroman-7-ylacetic acid, 4-(4-fluorophenylsulphonylaminomethyl)chroman-7-ylacetic acid, 4-(4-methylphenylsulphonylaminomethyl)chroman-7-ylacetic acid, 4-(3-chlorophenylsulphonylaminomethyl)chroman-7-ylacetic acid, 4-(phenylsulphonylamino)-2,2-dimethylchroman-7-yloxyacetic acid, 4-(4-ethylphenylsulphonylamino)-2,2-dimethylchroman-7-yloxyacetic acid, 4-(4-methoxyphenylsulphonylamino)-2,2-dimethylchroman-7-yloxyacetic acid, 4-(4-cyanophenylsulphonylamino)-2,2-dimethylchroman-7-yloxyacetic acid, 4-(3-fluorophenylsulphonylamino)-2,2-dimethylchroman-7-yloxyacetic acid, 4-(3-chlorophenylsulphonylamino)-2,2-dimethylchroman-7-yloxyacetic acid, 4-(3-methylphenylsulphonylamino)-2,2-dimethylchroman-7-yloxyacetic acid, 4-(phenylsulphonylaminomethyl)-2,2-spirocyclopentylchroman-7-yloxyacetic acid, 4-(4-fluorophenylsulphonylaminomethyl)-2,2-spirocyclopentylchroman-7-yloxyacetic acid, 4-(4-methylphenylsulphonylaminomethyl)-2,2-spirocyclopentylchroman-7-yloxyacetic acid, 4-(4-fluorophenylsulphonylamino)-2,2-spirocyclohexylchroman-7-yloxyacetic acid, 4-(phenylsulphonylaminomethyl)-2,2-spirocyclohexylchroman-7-yloxyacetic acid, 4-(phenylsulphonylamino)chroman-8-yloxyacetic acid, 4-(4-chlorophenylsulphonylamino)chroman-8-yloxyacetic acid, 4-(3-fluorophenylsulphonylamino)chroman-8-yloxyacetic acid, 4-(4-methylphenylsulphonylamino)chroman-8-yloxyacetic acid, 4-phenylsulphonylamino)-2,2-dimethylchroman-8-yloxyacetic acid, 4-(4-fluorophenylsulphonylamino)-2,2-dimethylchroman-8-yloxyacetic acid, 4-(4-chlorophenylsulphonylamino)-2,2-dimethylchroman-8-yloxyacetic acid, 4-(4-methylphenylsulphonylamino)-2,2-dimethylchroman-8-yloxyacetic acid, 4-(phenylsulphonylamino)-2,2-spirocyclopentylchroman-8-yloxyacetic acid, 4-(4-fluorophenylsulphonylamino)-2,2-spirocyclopentylchroman-8-yloxyacetic acid, 4-(4-chlorophenylsulphonylamino)-2,2-spirocyclopentylchroman-8-yloxyacetic acid, 4-(4-methoxyphenylsulphonylamino)-2,2-spirocyclopentylchroman-8-yloxyacetic acid, 4-(4-fluorophenylsulphonylamino)-2-phenylchroman-8-yloxyacetic acid, 4-(4-chlorophenylsulphonylamino)-2-phenylchroman-8-yloxyacetic acid, 4-(phenylsulphonylamino)chroman-7-ylacetic acid, 4-(4-fluorophenylsulphonylamino)chroman-7-ylacetic acid, 4-(4-chlorophenylsulphonylamino)chroman-7-ylacetic acid, 4-(3-fluorophenylsulphonylamino)chroman-7-ylacetic acid, 4-(4-methylphenylsulphonylamino)chroman-7-ylacetic acid, 4-(4-cyanophenylsulphonylamino)chroman-7-ylacetic acid, 4-(phenylsulphonylamino)chroman-8-ylacetic acid, 4-(4-fluorophenylsulphonylamino)chroman-8-ylacetic acid, 4-(4-chlorophenylsulphonylamino)chroman-8-ylacetic acid, 4-(4-methylphenylsulphonylamino)chroman-8-ylacetic acid, 4-(4-methoxyphenylsulphonylamino)chroman-8-ylacetic acid, 4-(4-trifluoromethylphenylsulphonylamino)chroman-8-ylacetic acid, 4-(3-fluorophenylsulphonylamino)chroman-8-ylacetic acid, 4-(4-fluorophenylsulphonylaminomethyl)chroman-8-ylthioacetic acid, 4-(4-fluorophenylsulphonylamino) 2,2-dimethylchroman-7-ylthioacetic acid, 4-(4-chlorophenylsulphonylaminomethyl)chroman-7-ylthioacetic acid and 4-(4-fluorophenylsulphonylamino)chroman-8-ylthioacetic acid.

It has furthermore been found that the new chroman derivatives of the general formula (I) are obtained when amines of the general formula (II)

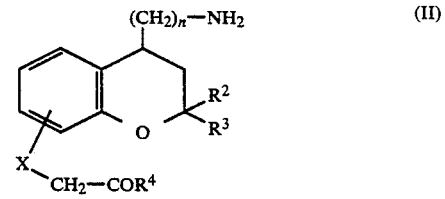

in which
$R^2$, $R^3$, $R^4$, X and n have the meaning indicated above,
are reacted in a manner known per se with sulphonic acids of the general formula (III)

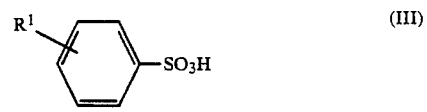

where
$R^1$ possesses the meaning indicated above, or their activated derivatives such as acid chlorides or activated esters.

In the case of R⁴≠OH, hydrolysis to the free carboxylic acids follows and then in the case of the preparation of the salts, reaction with the corresponding bases.

The amines of the general formula (II), in which R², R³, R⁴ and X have the abovementioned meanings and n is 1, are new. They are obtained from the corresponding α,β-unsaturated nitriles of the formula (IV)

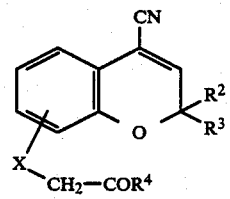
(IV)

in which

R², R³, R⁴ and X have the abovementioned meanings, by catalytic hydrogenation in the presence of NH₃. The hydrogenation can preferably be carried out by processes which are known in the literature (see, for example, Rylander, "Catalytic Hydrogenation", Academic Press, Inc., New York, 1967).

The new α,β-unsaturated nitriles (IV) are obtained from the chromanones of the general formula (V)

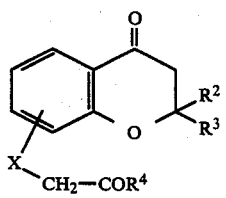
(V)

where

R², R³, R⁴ and X possess the meanings indicated above,
by reaction with trimethylsilyl cyanide, if appropriate in the presence of a catalyst, where the silylated cyanohydrins, which are directly reacted with acids to give the α,β- unsaturated nitriles of the formula (IV), result (compare lit.: D. A. Evans, G. L. Carroll and L. H. Truesdale, J. Org. Chem. 39, 914 (1974)).

The amines of the general formula (II), in which R², R³, R⁴ and X possess the meanings indicated above and n is 0, are new. They are also obtained from the chromanones of the general formula (V) by catalytic reductive amination analogously to processes which are known in the literature (for example J. Am. Chem. Soc. 93, 2897 (1971); Rylander, "Catalytic Hydrogenation", p. 291-303, Academic Press, Inc. New York, 1967; Org. Reactions 4, 174-255 (1948)) or by reductive amination using complex metal hydrides (compare Harada, in Patai, "The Chemistry of the Carbon-Nitrogen Double Bond", Interscience Publishers, New York, 1970, p. 276-293; J. Am. Chem. Soc. 93, 2897 (1971)).

The chromanones of the general formula (V), in which R², R³ and R⁴ possess the meanings indicated above and X stands for oxygen can be prepared from the hydroxychromanones of the general formula (VI)

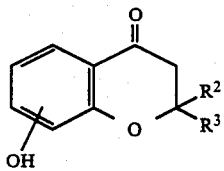
(VI)

in which

R² and R³ possess the meanings indicated above, by alkylation with acetic acid derivatives of the general formula (VII)

A—CH₂—COR⁴ (VII)

in which

A denotes a leaving group such as, for example,

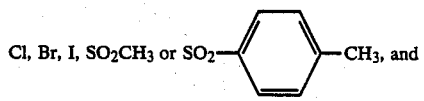

R⁴ possesses the meaning indicated above, according to processes which are known in the literature (for example Patai "The Chemistry of the Hydroxyl Group", pt. 1., p. 454–466, Interscience Publishers, New York, 1971; Tetrahedron 30, 1379 (1974)).

The hydroxy-4-chromanones of the general formula (VI), in which R² and R³ possess the meanings indicated above, are known in part or can be prepared from the known, corresponding methoxy-4-chromanones by ether cleavage analogously to processes which are known in the literature (for example J. M. Lockhart, in Ellis, "Chromenes, Chromanones and Chromones", Interscience Publication, New York, 1977, p. 207-428; J. Org. Chem. 14, p. 366 (1949); H. J. Kabbe, Synthesis 1978, 886).

The chromanones of the general formula (V), in which R², R³ and R⁴ possess the meanings indicated above and X stands for a bond, are known in part. They are obtained from the corresponding hydroxyphenylacetic acid derivatives of the general formula (VIII)

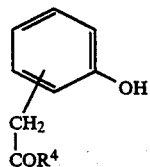
(VIII)

in which

R⁴ possesses the meaning indicated above, by processes which are known in the literature. Examples which may be mentioned are:

the addition of acrylonitrile to the phenolic hydroxyl group and subsequent cyclization—if necessary after previous hydrolysis to the carboxylic acid and conversion into the acid chloride—under Friedel-Crafts conditions. In this case, R² and R³ in the general formula (V) are equal to hydrogen (for example J. M. Lockhart, in Ellis, "Chromenes, Chromanones and Chromones", Interscience Publication, New York, 1977, 236-37)

the Friedel-Crafts acylation of the hydroxyphenylacetic acid derivatives (VIII) with acryloylchlorides of the general formula (IX)

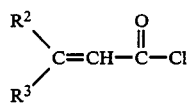  (IX)

in which

R² and R³ possess the meanings indicated above (for example J. M. Lockhart in Ellis, "Chromenes, Chromanones and Chromones", Interscience Publication, New York, 1977, p. 237–256)

the reaction of the corresponding substituted 2-hydroxyacetophenones (IX)

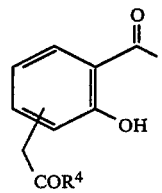  (X)

in which

R⁴ possesses the meaning indicated above, with carbonyl compounds of the general formula (XI)

  (XI)

in which

R² and R³ possess the meanings indicated above, in the presence of pyrrolidine (H. J. Kabbe, Synthesis 1978, 886).

When carrying out the process according to the invention, intermediates which can be isolated are in general formed. Thus, it is possible to carry out the process according to the invention in several process steps. However, it may also be possible to combine different process steps.

The final products I are obtained by reacting the amines of the general formula II with the corresponding sulphonic acids of the general formula (III), in which R¹ possesses the meaning indicated above, or their activated derivatives such as, for example, sulphonyl chlorides, sulphonic acid anhydrides or sulphonic acid esters in the presence of an acid-binding agent such as, for example, hydroxides or carbonates of alkali metals or of alkaline earth metals or organic bases such as, for example, triethylamine, pyridine or N-ethylmorpholine.

Depending on the type of sulphonic acid derivative employed, inert organic solvents such as, for example, methylene chloride, chloroform, ethyl acetate, tetrahydrofuran, ether, dimethylformamide and/or protic solvents such as, for example, water, methanol and ethanol are suitable as solvents.

The amines of the general formula II, in which R², R³, R⁴ and X possess the meaning indicated above and n is 1, are obtained by catalytic hydrogenation of α,β-unsaturated nitriles IV. Suitable catalysts are metals such as, for example, Raney nickel, palladium or platinum in the use forms known to those skilled in the art. Protic solvents such as, for example, methanol, ethanol and/or aprotic solvents such as, for example, tetrahydrofuran, toluene, dimethylformamide, methylene chloride or dioxane, to which liquid ammonia is expediently added, can serve as solvents. The hydrogenation is carried out at pressures between 5 and 300 atm, advantageously between 50 and 150 atm. The reaction temperature is between 20° and 150° C., advantageously between 30° and 100° C., and the reaction time is 15 minutes to 6 hours.

The β,β-unsaturated nitriles of the general formula IV are obtained from the chromanones V by reaction with trimethylsilyl cyanide. Suitable catalysts for this reaction are Lewis acids such as, for example, boron trifluoride etherate, zinc iodide, tin tetrachloride, aluminum trichloride or organic bases such as triethylamine, pyridine and also the complex from 18-crown-6 and potassium cyanide; the reaction may also be carried out without catalyst.

The reaction may be carried out in inert organic solvents such as diethyl ether, tetrahydrofuran, methylene chloride, toluene and also without solvents.

The reaction temperature is between 0° and 100° C., preferably between 20° and 60° C.

The crude silylated cyanohydrins are converted into the α,β-unsaturated nitriles IV by treating with acids. Suitable acids are organic acids such as, for example, trifluoroacetic acid, p-toluenesulphonic acid, formic acid, acetic acid or mineral acids such as hydrohalic acids, sulphuric acid or nitric acid. Alcohols such as, for example, methanol, ethanol, propanol or nonprotic solvents such as benzene, toluene, chlorinated hydrocarbons, tetrahydrofuran, dimethylformamide are suitable as solvents or the reaction is carried out without solvents.

The reaction temperature is between 0° and 120° C., preferably between 25° and 100° C., and the reaction time is between 10 minutes and 6 hours.

The amines of the general formula II, in which R², R³, R⁴ and X possess the meanings indicated above and n is 0, are obtained from the chromanones of the general formula V by reductive amination according to customary methods.

Suitable solvents in the amination are the customary organic solvents which do not change under the reaction conditions. These preferably include alcohols such as methanol, ethanol, propanol or isopropanol, or ethers such as diethyl ether, tetrahydrofuran or dioxane, or chlorinated hydrocarbons such as methylene chloride or chloroform, or acetonitrile, dimethylformamide, dimethyl sulphoxide, glacial acetic acid or mixtures of the solvents mentioned.

Suitable reductants are the customary complex hydrides such as, for example, sodium borohydride, sodium cyanoborohydride, or aminoborane complexes, and also hydrogen, if appropriate in the presence of a metal catalyst such as Raney nickel or palladium.

Aqueous ammonia solution, gaseous ammonia, or also ammonium salts such as ammonium chloride, ammonium sulphate, ammonium acetate or ammonium formate are employed as the ammonia-containing component.

The reaction can be carried out at atmospheric, at elevated or at reduced pressure (0.5 to 5 bar). In general, the reaction is carried out at atmospheric pressure when using complex metal hydrides, or with overpressure when using hydrogen.

The reductive amination is in general carried out in a temperature range from 0° C. to +150° C., preferably from +20° C. to +100° C.

Starting from the chromans V, the synthesis of the final products I can be summarized in the following reaction scheme:

(a) for n=1 in the general formula I

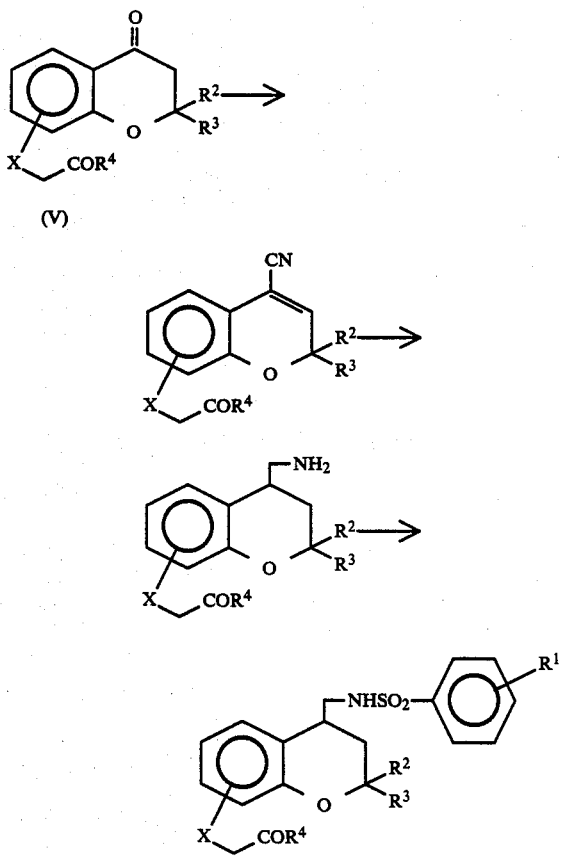

(b) for n=0 in the general formula I

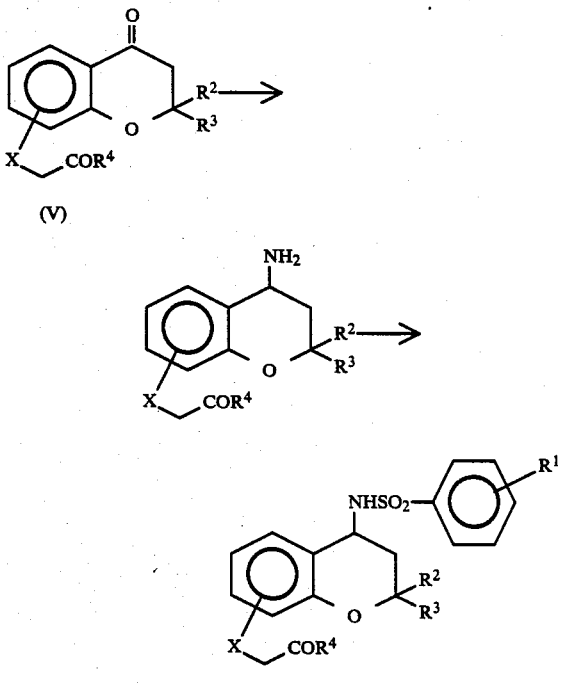

As examples of starting aminochromans of the general formula II there may be mentioned: 4-aminomethyl-7-chromanylacetic acid, 2,2-dimethyl-4-aminomethyl-7-chromanylacetic acid, 2,2-spirocyclopentyl-4-aminomethyl-7-chromanylacetic acid, 4-aminomethyl-8-chromanylacetic acid, 2,2-dimethyl-4-aminomethyl-8-chromanylacetic acid, 2,2-spirocyclopentyl-4-aminomethyl-8-chromanylacetic acid, 2,2-spirocyclohexyl-4-aminomethyl-8-chromanylacetic acid, 2-phenyl-4-aminomethyl-8-chromanylacetic acid, 4-aminomethyl-8-chromanyloxyacetic acid, 2,2-dimethyl-4-aminomethyl-8-chromanyloxyacetic acid, 2,2-diethyl-4-aminomethyl-8-chromanyloxyacetic acid, 2,2-spirocyclohexyl-4-aminomethyl-8-chromanyloxyacetic acid, 2-ethyl-4-aminomethyl-8-chromanyloxyacetic acid, 4-amino-7-chromanyloxyacetic acid, 2,2-dimethyl-4-amino-7-chromanyloxyacetic acid, 2,2-spirocyclopentyl-4-amino-7-chromanyloxyacetic acid, 4-aminomethyl-7-chromanyloxyacetic acid, 2,2-dimethyl-4-aminomethyl-7-chromanyloxyacetic acid, 2,2-diethyl-4-aminomethyl-7-chromanyloxyacetic acid, 2,2-spirocyclopentyl-4-aminomethyl-7-chromanyloxyacetic acid, 2,2-spirocyclohexyl-4-aminomethyl- 7-chromanyloxyacetic acid, 2-phenyl-4-aminomethyl-7-chromanyloxyacetic acid, 4-amino-8-chromanyloxyacetic acid, 2,2-dimethyl-4-amino-8-chromanyloxyacetic acid, 2,2-spirocyclopentyl-4-amino-8-chromanyloxyacetic acid, 2-phenyl-4-amino-8-chromanyloxyacetic acid, 4-amino-7-chromanylacetic acid, 2,2-dimethyl-4-amino-7-chromanylacetic acid, 2,2-spirocyclopentyl-4-amino-7-chromanylacetic acid, 4-amino-8-chromanylacetic acid, 2,2-dimethyl-4-amino-8-chromanylacetic acid and 2,2-spirocyclopentyl-4-amino-8-chromanylacetic acid.

The starting aminochromans of the general formula II are new.

The new substituted chromanyl derivatives or their salts can be employed as active compounds in medicaments. The active compounds exhibit a thrombocyte aggregation-inhibiting and also a vasodilatory and a bronchodilatory action. They can preferably be employed for the treatment of thromboses, thromboembolisms, ischaemias, as antiasthmatics and as antiallergics. The new active compounds may be converted in known manner into the customary formulations, such as tablets, dragees, pills, granules, aerosols, syrups, emulsions, suspensions and solutions, using inert, non-toxic, pharmaceutically suitable excipients or solvents. In this connection, the therapeutically active compound should in each case be present in a concentration from about 0.5 to 90% by weight of the total mixture, i.e. in amounts which are sufficient to achieve the indicated dosage range.

The formulations are prepared, for example, by extending the active compounds with solvents and/or excipients, if appropriate using emulsifiers and/or dispersing agents, where, for example, in the case of the use of water as a diluent, organic solvents may be used, if appropriate, as auxiliary solvents.

Auxiliaries which may be mentioned, for example, are: water, non-toxic organic solvents, such as paraffins (for example mineral oil fractions), vegetable oils (for example groundnut/sesame oil), alcohols (for example: ethyl alcohol, glycerol), excipients, such as, for example, ground natural minerals (for example clays, aluminas, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates and arylsulphonates), dispersing agents (for example lignin-sulphite waste liquors, methylcellulose, starch and polyvinylpyrrolidone) and lubricants (for example magnesium stearate, talc, stearic acid and sodium lauryl sulphate).

Administration takes place in a customary manner, preferably orally or parenterally, in particular perlingually or intravenously. In the case of oral administration, tablets may of course also contain additives, such as sodium citrate, calcium carbonate and dicalcium phosphate together with various supplementary substances, such as starch, preferably potato starch, gelatin and the like, in addition to the excipients mentioned. Furthermore, lubricants, such as magnesium stearate, sodium lauryl sulphate and talc can also be used for tabletting. In the case of aqueous suspensions, various flavor improvers or colorants may be added to the active compounds in addition to the abovementioned auxiliaries.

In general, it has proved advantageous on intravenous administration to administer amounts of about 0.001 to 1 mg/kg, preferably about 0.01 to 0.5 mg/kg of body weight to obtain efficacious results, and on oral administration the dosage is about 0.01 to 20 mg/kg, preferably 0.1 to 10 mg/kg of body weight.

In spite of this, it may be necessary to depart from the amounts mentioned, depending on the body weight or the type of administration route, on individual behavior towards the medicament, the manner of its formulation and point in time or interval which the administration takes place. Thus in some cases it may be sufficient to manage with less than the previously mentioned minimum amount, whereas in other cases the upper limit mentioned must be exceeded. In the case of the administration of larger amounts, it may be advisable to divide these into several individual doses over the day.

METHODOLOGY

Thrombocyte aggregation inhibition in vitro

For the in vitro determination of the thrombocyte aggregation-inhibiting action, blood from healthy donors, who had taken no medicament for at least 14 days, is used. The blood is taken up in 3.8% strength sodium citrate solution. Platelet-rich plasma (PRP) is obtained by centrifugation at 150 g at room temperature for 20 minutes (Jürgens/Beller: Klinische Methoden der Blutgerinnungsanalyse (Clinical Methods of Blood Coagulation Analysis); Thieme Verlag, Stuttgart 1959). The platelet aggregation is determined in an aggregometer at 37° C. by the turbidometric method (Born, G. V. R.: J. Physiol. 162, 67, 1962). For this, PRP is incubated at 37° C. with the test substance and aggregation is subsequently initiated by addition of a collagen suspension. For the in vitro tests, the minimum effective concentration of active compound (MEC) which inhibits the thrombocyte aggregation in the corresponding PRP samples is indicated.

TABLE

| Example No. | Inhibition of platelet aggregation (in vitro) Limit concentration (mg/l) |
|---|---|
| 28 | <0,03 |
| 29 | <0,03 |
| 30 | 0,01–0,03 |
| 31 | 0,3 |
| 32 | 3–10 |
| 33 | 10–30 |
| 34 | 0,01–0,1 |
| 35 | 0,03–0,01 |

TABLE-continued

| Example No. | Inhibition of platelet aggregation (in vitro) Limit concentration (mg/l) |
|---|---|
| 36 | 0,03–0,1 |
| 37 | 0,1–0,3 |
| 38 | 0,03–0,1 |
| 39 | 1–10 |

Thrombocyte aggregation inhibition ex vivo

For the vivo investigations, the active substance is orally administered to the animals in a Tylose suspension. After 90 minutes, the animals are exsanguinated and the PRP is obtained by means of centrifugation. The measurement of aggregation inhibition takes place analogously to the process which is described for the in vitro tests; however there is no preincubation of the samples.

PREPARATION EXAMPLES

Example 1

Methyl 4-cyanochrom-3-en-7-ylacetate

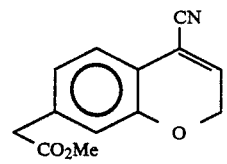

Several drops of BF₃ etherate are added to 5.85 g (25 mmol) of methyl chroman-4-on-7-yl-acetate and 7.43 g (75 mmol) of trimethylsilyl cyanide and the mixture is stirred at room temperature until the ketone band at 1690 cm$^{-1}$ in the IR has disappeared (about 45 minutes). 25 ml of trifluoroacetic acid are added and the mixture is heated to reflux for 2 hours. The trifluoroacetic acid is stripped off in a water-jet vacuum, the residue is taken up in 50 ml of methylene chloride and washed until neutral with saturated sodium hydrogen carbonate solution. The mixture is then washed once with saturated sodium chloride solution, dried over sodium sulphate and the drying agent is filtered off and the solution is evaporated. The residue is recrystallized from ligroin.

M.p.: 65° C.; yield: 3.55 g (41.5% of theory)

Example 2

Methyl 2,2-dimethyl-4-cyanochrom-3-en-7-yl-acetate

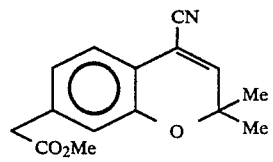

Preparation from methyl 2,2-dimethylchroman-4-on-7-yl-acetate analogously to Example 1.

M.p.: 61° C., yield: 53.3% of theory.

Example 3

Methyl 4-cyanochrom-3-en-8-yl-oxyacetate

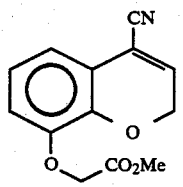

Preparation from methyl chroman-4-on-8-yl-oxyacetate analogously to Example 1.
M.p.: 94°–96° C., yield: 57.5% of theory.

Example 4

Methyl 4-cyanochrom-3-en-7-yloxyacetate

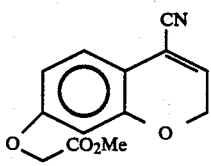

Preparation from methyl chroman-4-on-7-yl-oxyacetate analogously to Example 1.
M.p.: 104° C., yield: 67%.

Example 5

Methyl 2,2-dimethyl-4-cyanochrom-3-en-7-yl-oxyacetate

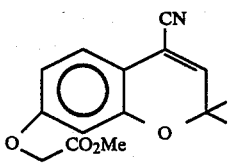

Preparation from methyl 2,2-dimethylchroman-4-on-7-yl-oxyacetate analogously to Example 1.
M.p.: 78°–79° C., yield: 71.6% of theory.

Example 6

Methyl 2,2-spirocyclopentyl-4-cyanochrom-3-en-7-yl-oxyacetate

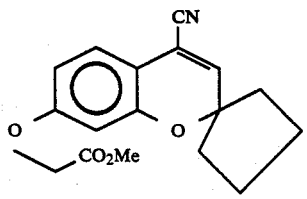

Preparation from methyl 2,2-spirocyclopentylchroman-4-on-7-yl-oxyacetate analogously to Example 1.
M.p.: 81° C., yield: 68.7% of theory.

Example 7

Methyl 2,2-spirocyclohexyl-4-cyanochrom-3-en-7-yl-oxyacetate

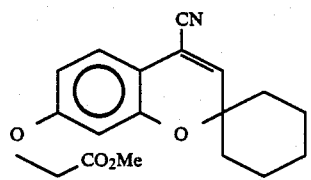

Preparation from methyl 2,2-spirocyclohexylchroman-4-on-7-yl-oxyacetate analogously to Example 1.
M.p.: 72°–75° C., yield: 59.8% of theory.

Example 8

4-Aminomethylchroman-7-yl-acetamide

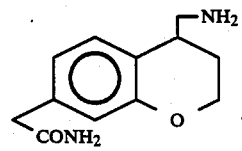

9.93 g (43.4 mmol) of nitrile from Example 1 in 100 ml of methanol and 80 ml of liquid ammonia are hydrogenated for 4.5 hours at 70° C. and 100 atm. using hydrogen in the presence of 5 g of Raney nickel. The catalyst is filtered off, boiled once with 100 ml of methanol and the combined methanol solutions are evaporated. The residue is chromatographed on silica gel at 2 bar using a mixture of methylene chloride and methanol as eluent in a ratio of 10:1. After evaporating the eluent, the product remains as a foam.

IR (CHCl$_3$): 1655 cm$^{-1}$ (amide); $^1$H-NMR (CDCl$_3$): $\delta=3.4$ (s, 2H) (CH$_2$ group next to amide).
Yield: 4.37 g (48.6%)

Example 9

2,2-Dimethyl-4-aminomethylchroman-7-yl-acetamide

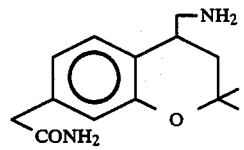

Preparation analogously to Example 8.
The unrecrystallized foam obtained after chromatography melts at 161° C. IR (CHCl$_3$): 1655 cm$^{-1}$; $^1$H-NMR (CDCl$_3$):$\delta=3.4$ (s, 2H). (CH$_2$ group next to amide).
Yield: 40.7% of theory.

Example 10

4-Aminochroman-8-yl-oxyacetamide

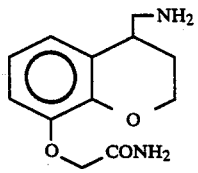

Preparation analogously to Example 8. Chromatographed using acetone/methanol in a ratio of 5:1.

IR(CHCl$_3$): 1670 cm$^{-1}$ (amide); $^1$H-NMR (CDCl$_3$): δ=4.45 (s, 2H) (CH$_2$ group next to amide).
Yield: 53.1% of theory.

Example 11

4-Aminomethylchroman-7-yl-oxyacetamide

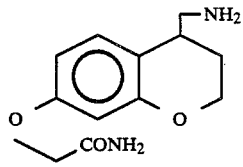

Preparation analogously to Example 8.
IR CHCl$_3$): 1675 cm$^{-1}$ (amide); $^1$H-NMR: (CDCl$_3$) δ=4.45 (s, 2H) (CH$_2$ group next to amide)
Yield: 58.2% of theory.

Example 12

2,2-Dimethyl-4-aminomethylchroman-7-yl-oxyacetamide

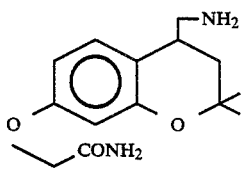

Preparation analogously to Example 8.
IR (CHCl$_3$): 1675 cm$^{-1}$ (amide); $^1$H-NMR (CDCl$_3$) δ=4.45 (s, 2H) (CH$_2$ group next to amide)
Yield: 75.8% of theory.

Example 13

2,2-Spirocyclopentyl-4-aminomethylchroman-7-yl-oxyacetamide

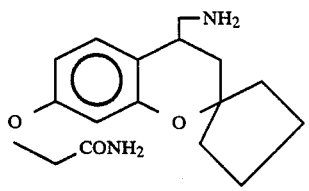

Preparation analogously to Example 8.
IR (CHCl$_3$): 1675 cm$^{-1}$ (amide); $^1$H-NMR: (CDCl$_3$) δ=4.47 (s, 2H) (CH$_2$ group next to amide); δ=1.4–2.1 (m, 12H)
Yield: 71.5% of theory.

Example 14

2,2-Spirocyclohexyl-4-aminomethylchroman-7-yl-oxyacetamide

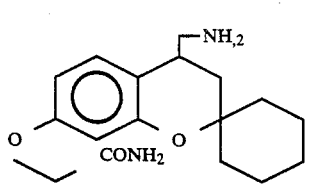

Preparation analogously to Example 8.

IR (CHCl$_3$): 1675 cm$^{-1}$ (amide); $^1$H-NMR (CDCl$_3$): δ=4.4 (s, 2H) (CH$_2$ group next to amide), δ=1.35–2.1 (m, 14H).

Example 15

2,2-Dimethyl-4-aminochroman-7-yloxyacetamide

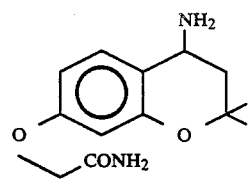

50 g (0.2 mol) of methyl 2,2-dimethylchroman-4-on-7-yl-oxyacetate in 200 ml of methanol and 250 ml of liquid ammonia are reductively aminated for 11 hours at 110° C. and 100 bar H$_2$ in the presence of 15 g of Raney nickel and 1 g of ammonium acetate. The catalyst is filtered off and boiled with methanol. Further working up takes place analogously to Example 8.

IR (CHCl$_3$): 1675 cm$^{-1}$ (amide); $^1$H-NMR (CDCl$_3$): δ=1.25 (s, 3H); 1.4 (s, 3H) (methyl groups in 2-position); δ=4.45 (CH$_2$ group next to amide). M.p.: 125° C. (from toluene).

Yield: 23.55 g (47.1%).

Example 16

4-(4-Chlorophenylsulphonylaminomethyl)chroman-7-yl-acetamide

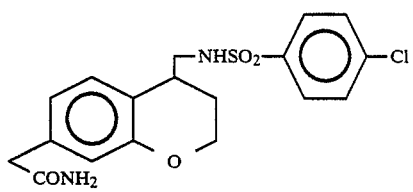

2.48 g (10 mmol) of 4-aminomethylchroman-7-ylacetamide are stirred for 2 to 3 hours at room temperature together with 2.53 g (12 mmol) of 4-chlorobenzenesulphonyl chloride in 10 ml of pyridine to which a spatula tip full of dimethylaminopyridine is added. The solution is added to 50 ml of ice-cold 10% HCl and extracted by shaking three times with ethyl acetate. The combined ethyl acetate phases are washed once with 10% HCl, once with saturated NaHCO$_3$ solution and once with saturated NaCl solution, dried over sodium sulphate and evaporated. The residue is chromatographed on silica gel using methylene chloride/methanol in a ratio of 10:1. After evaporating the eluent, the product remains as a solid. M.p.: 165°–70° C. (not recrystallized); $^1$H-NMR (CDCl$_3$): δ=3.45 (s, 2H), yield: 2.48 g (63% of theory).

Example 17

4-(4-Fluorophenylsulphonylaminomethyl)chroman-7-yl-acetamide

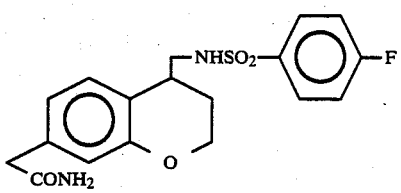

Preparation from 4-aminomethylchroman-7-yl-acetamide and 4-fluorobenzenesulphonyl chloride analogously to Example 16.
$^1$H-NMR (CDCl$_3$): δ=3.48 (s, 2H)
Yield: 58.3% of theory.

Example 18

4-(4-Chlorophenylsulphonylaminomethyl)-2,2-dimethylchroman-7-yl-acetamide

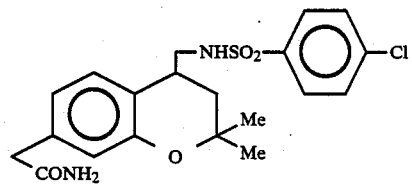

Preparation from 2,2-dimethyl-4-aminomethylchroman-7-yl-acetamide and 4-chlorobenzenesulphonyl chloride analogously to Example 16.
M.p.: 74°–78° C. (not recrystallized).
Yield: 67.9% of theory.

Example 19

4-(4-Fluorophenylsulphonylaminomethyl)chroman-8-yl-oxyacetamide

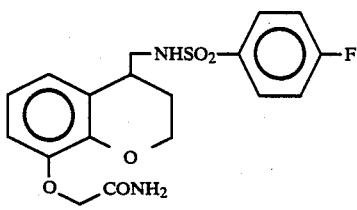

Preparation from 4-aminomethylchroman-8-yl-oxyacetamide and 4-fluorobenzenesulphonyl chloride analogously to Example 16.
M.p.: 137° C. (not recrystallized).
Yield: 41.9% of theory.

Example 20

4-(4-Chlorophenylsulphonylamino)-2,2-dimethylchroman-7-yl-oxyacetamide

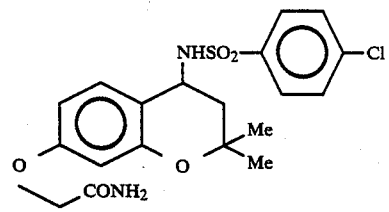

Preparation from 4-amino-2,2-dimethylchroman-7-yl-oxyacetamide and 4-chlorobenzenesulphonyl chloride analogously to Example 16. M.p.: 177°–180° C. (recrystallized after chromatography on toluene/petroleum ether).
Yield: 48.6% of theory.

EXAMPLE 21

4-(4-Fluorophenylsulphonylamino)-2,2-dimethylchroman-7-yl-oxyacetamide

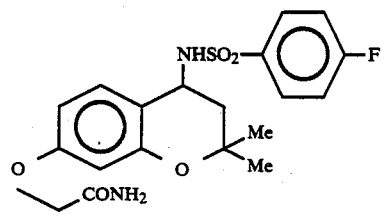

Preparation from 4-amino-2,2-dimethylchroman-7-yl-oxyacetamide and 4-fluorobenzenesulphonyl chloride analogously to Example 16.
M.p.: 191° C. (recrystallized after chromatography on toluene/petroleum ether).
Yield: 33.8% of theory.

Example 22

4-(4-Chlorophenylsulphonylaminomethyl)chroman-7-yl-oxyacetamide

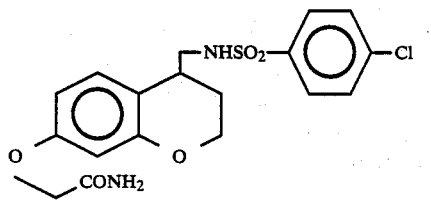

Preparation from 4-aminomethylchroman-7-yl-oxyacetamide and 4-chlorobenzenesulphonyl chloride analogously to Example 16.
M.p 80°–85° C. (not recrystallized).
Yield: 58.2% of theory.

Example 23

4-(4-Chlorophenylsulphonylaminomethyl)-2,2-dimethylchroman-7-yl-oxyacetamide

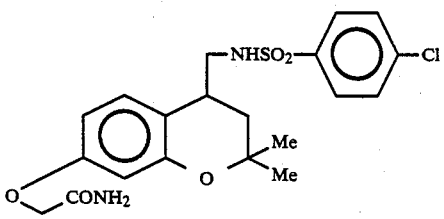

Preparation from 4-aminomethyl-2,2-dimethylchroman-7-yl-oxyacetamide and 4-chlorobenzenesulphonyl chloride analogously to Example 16.
M.p.: 178° C. (boiled with toluene after chromatography, product remains as clean undissolved material).
Yield: 62.9% of theory.

Example 24

4-(4-Fluorophenylsulphonylaminomethyl)-2,2-dimethylchroman-7-yl-oxyacetamide

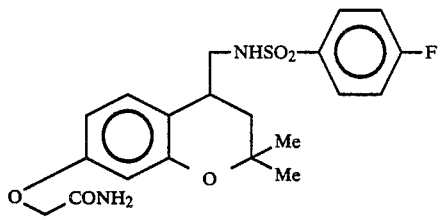

Preparation from 4-aminomethyl-2,2-dimethylchroman-7-yl-oxyacetamide and 4-fluorobenzenesulphonyl chloride analogously to Example 16. IR (KBr): 1680 cm$^{-1}$ (CON); 1330 cm$^{-1}$ (SO$_2$N); 1170 cm$^{-1}$ IR (KBr): 1680 cm (SO$_2$N).

Yield: 71.8% of theory.

Example 25

4-(4-Methylphenylsulphonylaminomethyl)-2,2-dimethylchroman-7-yl-oxyacetamide

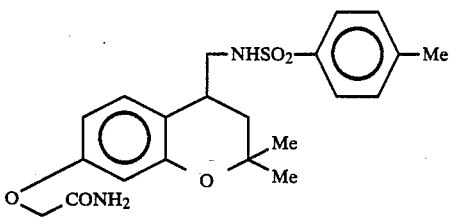

Preparation 4-aminomethyl-2,2-dimethylchroman-7yl-oxyacetate and 4-methylbenzenesulphonyl chloride analogously to Example 16.

IR (KBr): 1660 cm$^{-1}$ (CON); 1320 cm$^{-1}$ (SO$_2$N); 1170 cm$^{-1}$ (SO$_2$N).

Yield: 60.2% of theory.

Example 26

4-(4-Chlorophenylsulphonylaminomethyl)-2,2-spirocyclopentylchroman-7-yl-oxyacetamide

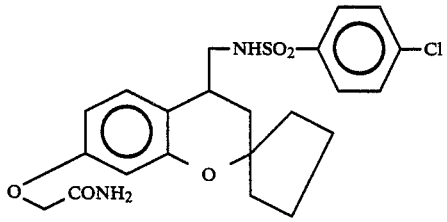

Preparation from 4-aminomethyl-2,2-spirocyclo-pentylchroman-7-yloxyacetamide and 4-chlorobenzenesulphonyl chloride analogously to Example 16.

IR (CH$_2$Cl$_2$): 1690 cm$^{-1}$ (CON); 1340 cm$^{-1}$ (SO$_2$N); 1160 cm$^{-1}$ (SO$_2$N).

Yield: 61.9% of theory.

Example 27

4-(4-Chlorophenylsulphonylaminomethyl)-2,2-spirocyclohexylchroman-7-yl-oxyacetamide

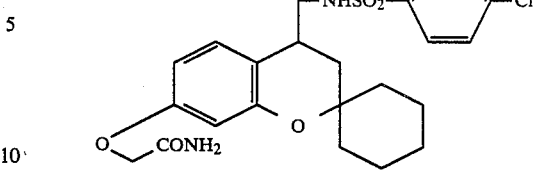

Preparation from 4-aminomethyl-2,2-spirocyclohexylchroman-7-yl-oxyacetamide and 4-chlorobenzenesulphonyl chloride analogously to Example 16.

IR (CH$_2$Cl$_2$): 1690 cm$^{-1}$ (CON); 1330 cm$^{-1}$ (SO$_2$N); 1160 cm$^{-1}$ (SO$_2$N).

Yield: 70.8% of theory.

Example 28

4-(4-Chlorophenylsulphonylaminomethyl)chroman-7-yl-acetic acid

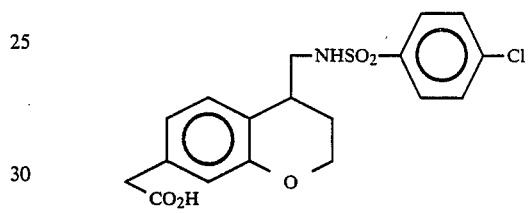

3.945 g (10 mmol) of 4-(4-chlorophenylsulphonylaminomethyl)chroman-7-yl-acetamide and 25 ml of 1N KOH are refluxed for 5 hours after the addition of 50 ml of methanol. The methanol is removed by evaporation in a water-jet vacuum, and the aqueous phase is extracted by shaking once with ethyl acetate and then brought to pH 1–2 using concentrated hydrochloric acid. The precipitate is filtered off the aqueous phase is extracted by shaking twice with ethyl acetate, and the combined ethyl acetate phases are dried over sodium sulphate and then evaporated. The residue is combined with the precipitate filtered off and dried in a high vacuum. The acids are clean without recrystallization or chromatography.

IR (film): 1710 cm$^{-1}$ (COOH); $^1$H-NMR (CD$_3$OD): δ=3.4 (s, 2H) (CH$_2$ group next to COOH).

Yield: 3.28 g (83% of theory).

Example 29

4-(4-Fluorophenylsulphonylaminomethyl)chroman-7-yl-acetic acid

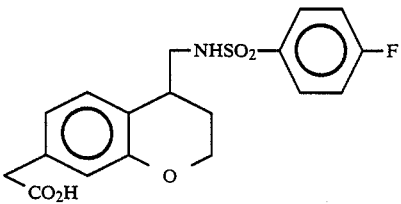

Preparation from the corresponding amide by hydrolysis analogously to Example 28.

M.p.: 57°–60° C. (not recystallized); $^1$H-NMR (CD$_3$OD): δ=3.4 (s, 2H) (CH$_2$ group next to COOH).

Example 30

4-(4-Chlorophenylsulphonylaminomethyl)-2'2-dimethyl-chroman-7-yl-acetic acid

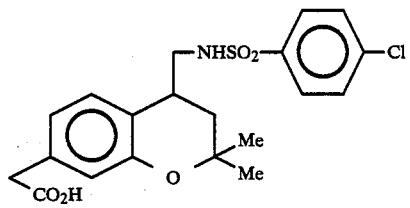

Preparation from the corresponding amide by hydrolysis analogously to Example 28.

M.p.: 65°–70° C. (not recrystallized); $^1$H-NMR (CD$_3$OD): δ=3.4 (s, 2H) (CH$_2$ group next to COOH).

Example 31

4-(4-Fluorophenylsulphonylaminomethyl)chroman-8-yl-oxyacetic acid

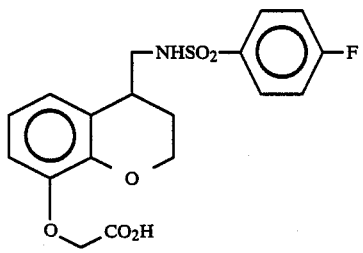

Preparation from the corresponding amide by hydrolysis analogously to Example 28.

M.p.: 110° C. (not recrystallized); IR (KBr): 1740 cm$^{-1}$ (COOH).

Yield: 76.4% of theory.

Example 32

4-(4-Chlorophenylsulphonylamino)-2,2-dimethylchroman-7-yl-oxyacetic acid

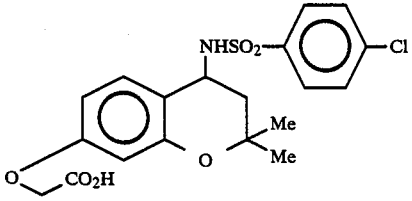

Preparation from the corresponding amide by hydrolysis analogously to Example 28.

M.p.: 167° C. (recrystallized from toluene/petroleum ether)

Yield: 58.9% of theory

Example 33

4-(4-Fluorophenylsulphonylamino)-2,2-dimethylchroman-7-yl-oxyacetic acid

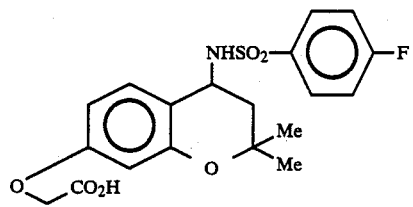

Preparation from the corresponding amide by hydrolysis analogously to Example 28.

M.p.: 174° C. (recrystallized from toluene/petroleum ether)

Yield: 94% of theory

Example 34

4-(4-Chlorophenylsulphonylaminomethyl)chroman-7-yl-oxyacetic acid

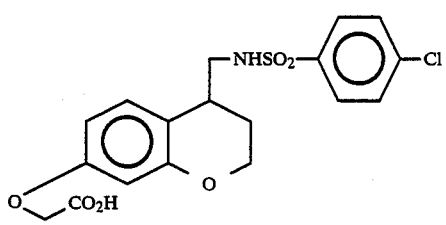

Preparation from the corresponding amide by hydrolysis analogously to Example 28.

$^1$H-NMR (CDCl$_3$): δ=4.6 (s, 2H) (CH$_2$ group next to COOH); IR (CH$_2$Cl$_2$): 1740 cm$^{-1}$ (COOH)

Yield: 95.9% of theory

Example 35

4-(4-Chlorophenylsuphonylaminomethyl)-2,2-dimethylchroman-7-yl-oxyacetic acid

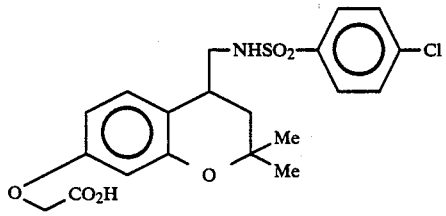

Preparation from the corresponding amide by hydrolysis analogously to Example 28.

$^1$H-NMR (CD$_3$OD): δ=4.5 (s, 2H) (CH$_2$ group next to COOH); IR (KBr): 1725 cm$^{-1}$ (COOH)

Yield: 98.9% of theory

Example 36

4-(4-Fluorophenylsulphonylaminomethyl)-2,2-dimethylchroman-7-yl-oxyacetic acid

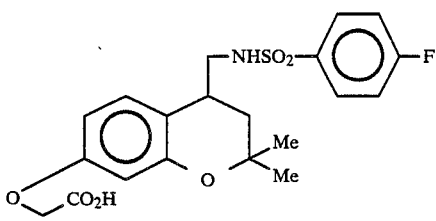

Preparation from the corresponding amide by hydrolysis analogously to Example 28.

M.p.: 173° C. (recrystallized from ethyl acetate/petroleum ether)

Yield: 74.5% of theory.

Example 37

4-(4-Methylphenylsulphonylaminomethyl)-2,2-dimethylchroman-7-yl-oxyacetic acid

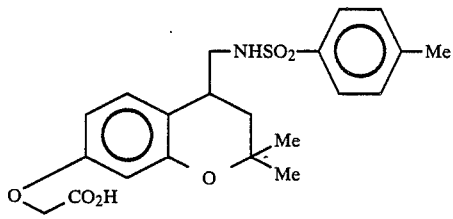

Preparation from the corresponding amide by hydrolysis analogously to Example 28.

M.p.: 123° C. (recrystallized from ethyl acetate/petroleum ether)

Yield: 87.1% of theory.

Example 38

4-(4-Chlorophenylsulphonylaminomethyl)-2,2-spirocyclopentylchroman-7-yl-oxyacetic acid

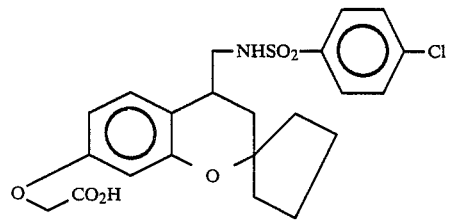

Preparation from the corresponding amide by hydrolysis analogously to Example 28. $^1$H-NMR (CDCl$_3$): $\delta = 6$ (s, 2H) (CH$_2$ group next to COOH)

IR (CH$_2$C$_{12}$ film): 1735 cm$^{-1}$ (COOH)

Yield: 80.1% of theory

Example 39

4-(4-Chlorophenylsulphonylaminomethyl)-2,2-spirocyclohexylchroman-7-yl-oxyacetic acid

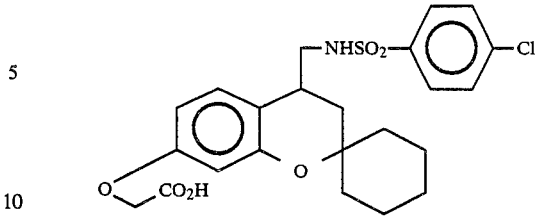

Preparation from the corresponding amide by hydrolysis analogously to Example 28.

M.p.: 64°–68° C. (not recrystallized).

$^1$H-NMR (CD$_3$OD): $\delta = 4.6$ (s, 2H) (CH$_2$ group next to COOH)

Yield: 95.1% of theory.

It will be appreciated that the instant specification and claims are set worth by way of illustration and not limitation, and that various modifications and changes may be made without departing from the spirit and scope of the present invention.

What is claimed is:

1. A chroman derivative of the formula

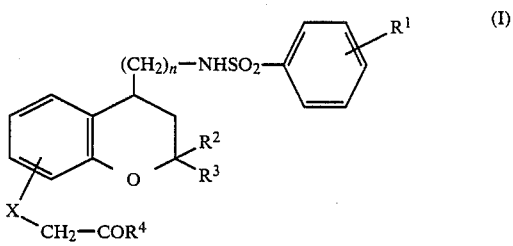

in which

R$^1$ stands for hydrogen, halogen, alkyl, hydroxyl, alkoxy, trifluoromethyl or cyano, R$^2$ and R$^3$ are identical or different and stand for hydrogen, alkyl, cycloalkyl or aryl, R$^4$ stands for hydroxyl, alkoxy, aryloxy, aralkoxy or for a group of the formula —NR$^5$R$^6$, where R$^5$ and R$^6$ are identical or different and in each case denote hydrogen, alkyl, aryl or aralkyl, X denotes a direct bond or an oxygen or sulphur atom, NH or N-alkyl, and n denotes 0 or 1, or a physiologically tolerable salt thereof.

2. A compound or salt according to claim 1, in which

R$^1$ stands for hydrogen, fluorine, chlorine, bromine, iodine, methyl, ethyl, propyl, isopropyl, hydroxyl, methoxy, ethoxy, propoxy, isopropoxy, trifluoromethyl or cyano, R$^2$ and R$^3$ are identical or different and stand for hydrogen, methyl, ethyl, propyl, isopropyl, cyclobutyl, cyclopentyl, cyclohexyl, cycloheptyl or phenyl, R$^4$ stands for hydroxyl, methoxy, ethoxy, phenoxy, benzyloxy or for a group of the formula —NR$^5$R$^6$, where R$^5$ and R$^6$ are identical or different and in each case denote hydrogen, methyl, ethyl, phenyl or benzyl, X stands for a direct bond or an oxygen or sulphur atom, n stands for 0 or 1.

3. A compound according to claim 1, wherein such compound is 4-(4-chlorophenylsulphonylaminomethyl)chroman-7-ylacetic acid of the formula

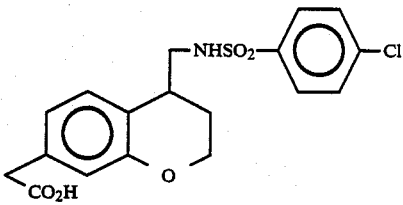

a physiologically tolerable salt thereof.

4. A compound according to claim 1, wherein such compound is 4-(4-florophenylsulphonylaminomethyl)-chroman-7-ylacetic acid of the formula

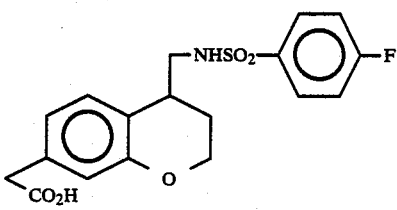

or a physiologically tolerable salt thereof.

5. A compound according to claim 1, wherein such compound is 4-(4-chlorophenylsulphonylrinomethyl 2,2-7-ylacetic acid of the formula

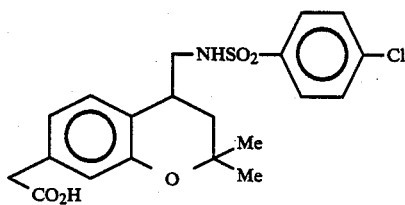

or a physiologically tolerable salt thereof.

6. A compound according to claim 1, wherein such compound is 4-(4-fluorophenylsulphonylaminomethyl)-chroman-8-yloxyacetic acid of the formula

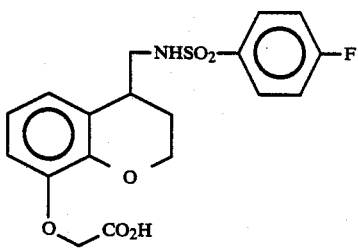

or a physiologically tolerable salt thereof.

7. A thrombocyte aggregation-inhibiting, vasodilating and bronchodilating composition comprising an amount effective therefor of a compound or salt thereof according to claim 1 and a physiologically tolerable diluent.

8. A method of inhibiting thrombocyte aggregation, vasodilating or bronchodilating a patient in need thereof which comprises administering to such patient an amount effective therefor or a compound or salt thereof according to claim 1.

9. The method according to claim 8, wherein such compound is
4-(4-chlorophenylsulphonylaminomethys)chroman-7-ylacetic acid,
(4-fluorophenylsulphonylaminomethyl)chroman-7-ylacetic acid,
(4-chloroPhenylsulphonylaminomethyl)chn-2,2-dimethyl-7-ylacetic acid, or
4-(4-fluorophenylsulphonylaminomethyl)chroman-8-yloxyacetic acid.

10. An amine of the formula

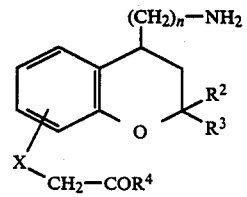

in which
$R^2$ and $R^3$ are identical or different and stand for hydrogen, alkyl, cycloalkyl or aryl,
$R^4$ stands for hydroxyl alkoxy, aryloxy, aralkoxy or for a group of the formula $-NR^5R^6$, where $R^5$ and $R^6$ are identical or different and in each case denote hydrogen, alkyl, aryl or aralkyl,
X denotes a direct bond or an oxygen or sulphur atom, NH or N-alkyl, and
n denotew 0 or 1.

11. A nitrile of the formula

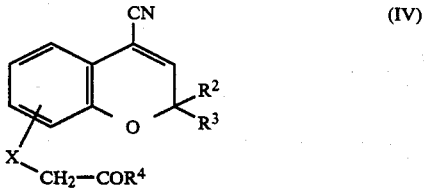

in which
$R^2$ and $R^3$ are identical or different and stand for hydrogen alkyl, cycloalkyl or aryl,
$R^4$ stands for hydroxyl, alkoxy, aryloxy, aralkoxy or for a group of the formula $-NR^5R^6$, where $R^5$ and $R^6$ are identical or different and in each case denote hydrogen, alkyl, aryl or aralkyl,
X denotes a direct bond or an oxygen or sulphur atom, NH or N-alkyl, and
n denotes 0 or 1.

* * * * *